(12) United States Patent
Wang et al.

(10) Patent No.: US 7,722,647 B1
(45) Date of Patent: May 25, 2010

(54) APPARATUS AND METHOD FOR POSTERIOR VERTEBRAL STABILIZATION

(75) Inventors: Jeffery C. Wang, Sherman Oaks, CA (US); T. Wade Fallin, Hyde Park, UT (US); Robert W. Hoy, Paradise, UT (US); Alan Chervitz, Palm Harbor, FL (US)

(73) Assignee: Facet Solutions, Inc., Hopkinton, MA (US)

( * ) Notice: Subject to any disclaimer, the term of this patent is extended or adjusted under 35 U.S.C. 154(b) by 212 days.

(21) Appl. No.: 11/079,755

(22) Filed: Mar. 14, 2005

(51) Int. Cl.
*A61B 17/70* (2006.01)
(52) U.S. Cl. .................. 606/247; 606/246; 606/61
(58) Field of Classification Search .............. 606/61, 606/246–249; 623/17.11–17.16, 22.21–22.39
See application file for complete search history.

(56) References Cited

U.S. PATENT DOCUMENTS

| | | | |
|---|---|---|---|
| 2,677,369 A | 5/1954 | Knowles | |
| 3,247,000 A | 4/1966 | Taylor | |
| 3,298,372 A | 1/1967 | Feinberg | |
| 3,426,364 A | 2/1969 | Lumb | |
| 3,486,505 A | 12/1969 | Morrison | |
| 3,508,954 A | 4/1970 | White et al. | |
| 3,648,691 A | 3/1972 | Lumb et al. | |
| 3,857,642 A | 12/1974 | Miller | |
| 3,867,728 A | 2/1975 | Stubstad et al. | |
| 3,875,595 A | 4/1975 | Froning | |
| 4,003,376 A | 1/1977 | McKay | |
| 4,092,078 A | 5/1978 | Klotz et al. | |
| 4,289,123 A | 9/1981 | Dunn | |
| 4,349,921 A | 9/1982 | Kuntz | |
| 4,369,769 A | 1/1983 | Edwards | |
| 4,479,491 A | 10/1984 | Martin | |
| 4,483,334 A | 11/1984 | Murray | |
| 4,501,269 A | 2/1985 | Bagby | |

(Continued)

FOREIGN PATENT DOCUMENTS

CN        2386790 Y        7/2000

(Continued)

OTHER PUBLICATIONS

Impliant ; *Posterior Fixation Website*; www.impliant.com.

(Continued)

*Primary Examiner*—Eduardo C Robert
*Assistant Examiner*—Christina Negrelli
(74) *Attorney, Agent, or Firm*—Daniel F. Justin; Barbara Daniels; G. Jo Hays

(57) ABSTRACT

A facet joint replacement implant may have a posterior stabilization surface designed to restrict posterior motion of a vertebra with respect to an adjacent, inferior vertebra. The facet joint replacement implant replaces the natural articular surface of one of the vertebrae, and articulates with a natural articular surface or with an articular surface of a second implant on the other vertebra. The posterior stabilization surface may be on a posterior flange of a superior facet joint implant, which extends posteriorly of a corresponding inferior facet joint implant. The inferior facet joint implant has an abutment surface that abuts the posterior stabilization surface as the superior vertebra begins to move posteriorly with respect to the inferior vertebra, thereby limiting the posterior motion.

20 Claims, 2 Drawing Sheets

U.S. PATENT DOCUMENTS

| | | | |
|---|---|---|---|
| 4,554,914 A | 11/1985 | Kapp et al. | |
| 4,599,086 A | 7/1986 | Doty | |
| 4,604,995 A | 8/1986 | Stephens et al. | |
| 4,611,581 A | 9/1986 | Steffee | |
| 4,641,636 A | 2/1987 | Cotrel | |
| 4,653,481 A | 3/1987 | Howland et al. | |
| 4,657,550 A | 4/1987 | Daher | |
| 4,696,290 A | 9/1987 | Steffee | |
| 4,743,260 A | 5/1988 | Burton | |
| 4,759,769 A | 7/1988 | Hedman et al. | |
| 4,772,287 A | 9/1988 | Ray et al. | |
| 4,790,303 A | 12/1988 | Steffee | |
| 4,800,874 A | 1/1989 | David et al. | |
| 4,805,602 A | 2/1989 | Puno et al. | |
| 4,827,918 A | 5/1989 | Olerud | |
| 4,863,476 A | 9/1989 | Shepperd | |
| 4,863,477 A | 9/1989 | Monson | |
| 4,892,545 A | 1/1990 | Day et al. | |
| 4,904,260 A | 2/1990 | Ray et al. | |
| 4,911,718 A | 3/1990 | Lee et al. | |
| 4,946,458 A | 8/1990 | Harms et al. | |
| 4,955,908 A | 9/1990 | Frey et al. | |
| 5,011,484 A | 4/1991 | Breard | |
| 5,015,255 A | 5/1991 | Kuslich | |
| 5,047,055 A | 9/1991 | Bao et al. | |
| 5,071,437 A | 12/1991 | Steffee | |
| 5,092,866 A | 3/1992 | Breard et al. | |
| 5,092,867 A | 3/1992 | Harms et al. | |
| 5,092,893 A | 3/1992 | Smith | |
| 5,127,912 A | 7/1992 | Ray et al. | |
| 5,129,900 A | 7/1992 | Asher et al. | |
| 5,147,361 A | 9/1992 | Ojima et al. | |
| 5,147,404 A | 9/1992 | Downey | |
| 5,171,279 A | 12/1992 | Mathews | |
| 5,171,280 A | 12/1992 | Baumgartner | |
| 5,180,393 A | 1/1993 | Commarmond | |
| 5,192,326 A | 3/1993 | Bao et al. | |
| 5,236,460 A | 8/1993 | Barber | |
| 5,246,458 A | 9/1993 | Graham | |
| 5,258,031 A | 11/1993 | Salib et al. | |
| 5,261,910 A | 11/1993 | Warden et al. | |
| 5,263,953 A | 11/1993 | Bagby | |
| 5,282,863 A | 2/1994 | Burton | |
| 5,304,178 A | 4/1994 | Stahurski | |
| 5,306,275 A | 4/1994 | Bryan | |
| 5,306,308 A | 4/1994 | Gross et al. | |
| 5,306,309 A | 4/1994 | Wagner et al. | |
| 5,313,962 A | 5/1994 | Obenchain | |
| 5,318,567 A | 6/1994 | Vichard | |
| 5,360,430 A | 11/1994 | Lin | |
| 5,366,455 A | 11/1994 | Dove et al. | |
| 5,370,697 A | 12/1994 | Baumgartner | |
| 5,375,823 A | 12/1994 | Navas | |
| 5,391,168 A | 2/1995 | Sanders et al. | |
| 5,401,269 A | 3/1995 | Buttner-Janz et al. | |
| 5,415,661 A | 5/1995 | Holmes | |
| 5,437,669 A | 8/1995 | Yuan et al. | |
| 5,437,672 A | 8/1995 | Alleyne | |
| 5,439,464 A | 8/1995 | Shapiro | |
| 5,443,516 A | 8/1995 | Albrektsson et al. | |
| 5,456,722 A | 10/1995 | McLeod et al. | |
| 5,458,641 A | 10/1995 | Ramirez Jimenez | |
| 5,458,642 A | 10/1995 | Beer et al. | |
| 5,458,643 A | 10/1995 | Oka et al. | |
| 5,464,439 A | 11/1995 | Gendler | |
| 5,470,333 A | 11/1995 | Ray | |
| 5,476,463 A | 12/1995 | Boachie-Adjei et al. | |
| 5,480,401 A | 1/1996 | Navas | |
| 5,489,308 A | 2/1996 | Kuslich et al. | |
| 5,496,318 A | 3/1996 | Howland et al. | |
| 5,507,745 A | 4/1996 | Logroscino et al. | |
| 5,507,813 A | 4/1996 | Dowd et al. | |
| 5,514,180 A | 5/1996 | Heggeness et al. | |
| 5,522,899 A | 6/1996 | Michelson | |
| 5,527,312 A | 6/1996 | Ray | |
| 5,531,745 A | 7/1996 | Ray | |
| 5,531,747 A | 7/1996 | Ray | |
| 5,534,028 A | 7/1996 | Bao et al. | |
| 5,534,030 A | 7/1996 | Navarro et al. | |
| 5,534,031 A | 7/1996 | Matsuzaki et al. | |
| 5,540,688 A | 7/1996 | Navas | |
| 5,545,166 A | 8/1996 | Howland | |
| 5,545,229 A | 8/1996 | Parsons et al. | |
| 5,549,607 A | 8/1996 | Olson et al. | |
| 5,556,431 A | 9/1996 | Buttner-Janz | |
| 5,556,687 A | 9/1996 | McMillin | |
| 5,562,735 A | 10/1996 | Margulies | |
| 5,562,736 A | 10/1996 | Ray et al. | |
| 5,562,737 A | 10/1996 | Graf | |
| 5,569,248 A | 10/1996 | Mathews | |
| 5,571,189 A | 11/1996 | Kuslich | |
| 5,571,191 A | 11/1996 | Fitz | |
| 5,572,191 A | 11/1996 | Lundberg | |
| 5,582,612 A | 12/1996 | Lin | |
| 5,584,832 A | 12/1996 | Schlapfer | |
| 5,603,713 A | 2/1997 | Aust et al. | |
| 5,609,634 A | 3/1997 | Voydeville | |
| 5,645,597 A | 7/1997 | Krapiva | |
| 5,645,599 A | 7/1997 | Samani | |
| 5,649,926 A | 7/1997 | Howland | |
| 5,653,762 A | 8/1997 | Pisharodi | |
| 5,666,243 A | 9/1997 | Brent | |
| 5,672,175 A | 9/1997 | Martin | |
| 5,674,295 A | 10/1997 | Ray et al. | |
| 5,674,296 A | 10/1997 | Bryan | |
| 5,676,701 A | 10/1997 | Yuan et al. | |
| 5,681,310 A | 10/1997 | Yuan et al. | |
| 5,683,464 A | 11/1997 | Wagner et al. | |
| 5,683,465 A | 11/1997 | Shinn et al. | |
| 5,688,272 A | 11/1997 | Montague et al. | |
| 5,690,629 A | 11/1997 | Asher et al. | |
| 5,702,392 A | 12/1997 | Wu et al. | |
| 5,702,450 A | 12/1997 | Bisserie | |
| 5,702,453 A | 12/1997 | Rabbe et al. | |
| 5,704,936 A | 1/1998 | Mazel | |
| 5,713,900 A | 2/1998 | Benzel et al. | |
| 5,716,415 A | 2/1998 | Steffee | |
| 5,725,582 A | 3/1998 | Bevan et al. | |
| 5,728,097 A | 3/1998 | Mathews | |
| 5,735,899 A | 4/1998 | Schwartz et al. | |
| 5,749,873 A | 5/1998 | Fairley | |
| 5,755,796 A | 5/1998 | Ibo et al. | |
| 5,772,661 A | 6/1998 | Michelson | |
| 5,797,909 A | 8/1998 | Michelson | |
| 5,814,046 A | 9/1998 | Hopf | |
| 5,824,093 A | 10/1998 | Ray et al. | |
| 5,824,094 A | 10/1998 | Serhan et al. | |
| 5,836,948 A | 11/1998 | Zucherman et al. | |
| 5,860,977 A | 1/1999 | Zucherman et al. | |
| 5,865,846 A | 2/1999 | Bryan et al. | |
| 5,868,745 A | 2/1999 | Alleyne | |
| 5,876,404 A | 3/1999 | Zucherman et al. | |
| 5,888,223 A | 3/1999 | Bray, Jr. | |
| 5,893,889 A | 4/1999 | Harrington | |
| RE36,221 E | 6/1999 | Breard et al. | |
| 5,916,267 A | 6/1999 | Tienboon | |
| 5,951,555 A | 9/1999 | Rehak et al. | |
| 5,961,516 A | 10/1999 | Graf | |
| 5,986,169 A | 11/1999 | Gjunter | |
| 6,001,130 A | 12/1999 | Bryan et al. | |
| 6,004,322 A | 12/1999 | Bernstein | |
| 6,014,588 A | 1/2000 | Fitz | |
| 6,019,759 A | 2/2000 | Rogozinski | |
| 6,019,792 A | 2/2000 | Cauthen | |

| | | | |
|---|---|---|---|
| 6,039,761 A | 3/2000 | Li et al. | |
| 6,039,763 A | 3/2000 | Shelokov | |
| 6,048,342 A | 4/2000 | Zucherman et al. | |
| 6,063,088 A | 5/2000 | Winslow | |
| 6,063,121 A | 5/2000 | Xavier et al. | |
| 6,066,325 A | 5/2000 | Wallace et al. | |
| 6,068,630 A | 5/2000 | Zucherman et al. | |
| RE36,758 E | 6/2000 | Fitz | |
| 6,074,390 A | 6/2000 | Zucherman et al. | |
| 6,080,157 A | 6/2000 | Cathro et al. | |
| 6,090,112 A | 7/2000 | Zucherman et al. | |
| 6,093,205 A | 7/2000 | McLeod et al. | |
| 6,113,637 A | 9/2000 | Gill et al. | |
| 6,113,639 A | 9/2000 | Ray et al. | |
| 6,132,464 A | 10/2000 | Martin | |
| 6,132,465 A | 10/2000 | Ray et al. | |
| 6,146,421 A | 11/2000 | Gordon et al. | |
| 6,149,652 A | 11/2000 | Zucherman et al. | |
| 6,151,934 A | 11/2000 | Chong et al. | |
| 6,152,926 A | 11/2000 | Zucherman et al. | |
| 6,156,038 A | 12/2000 | Zucherman et al. | |
| 6,156,067 A | 12/2000 | Bryan et al. | |
| 6,176,861 B1 | 1/2001 | Bernstein et al. | |
| 6,179,838 B1 | 1/2001 | Fiz | |
| 6,183,471 B1 | 2/2001 | Zucherman et al. | |
| 6,190,387 B1 | 2/2001 | Zucherman et al. | |
| 6,190,414 B1 | 2/2001 | Young et al. | |
| 6,206,882 B1 | 3/2001 | Cohen | |
| 6,206,922 B1 | 3/2001 | Zdeblick et al. | |
| 6,228,118 B1 | 5/2001 | Gordon | |
| 6,235,030 B1 | 5/2001 | Zucherman et al. | |
| 6,238,397 B1 | 5/2001 | Zucherman et al. | |
| 6,241,730 B1 | 6/2001 | Alby | |
| 6,264,655 B1 | 7/2001 | Pisharodi | |
| 6,267,764 B1 | 7/2001 | Elberg | |
| 6,280,444 B1 | 8/2001 | Zucherman et al. | |
| 6,290,700 B1 | 9/2001 | Schmotzer | |
| 6,293,949 B1 | 9/2001 | Justis et al. | |
| 6,312,469 B1 | 11/2001 | Gielen et al. | |
| 6,314,325 B1 | 11/2001 | Fitz | |
| 6,332,882 B1 | 12/2001 | Zucherman et al. | |
| 6,332,883 B1 | 12/2001 | Zucherman et al. | |
| 6,379,355 B1 | 4/2002 | Zucherman et al. | |
| 6,402,750 B1 | 6/2002 | Atkinson et al. | |
| 6,413,259 B1 | 7/2002 | Lyons et al. | |
| 6,419,676 B1 | 7/2002 | Zucherman et al. | |
| 6,419,677 B2 | 7/2002 | Zucherman et al. | |
| 6,419,703 B1 | 7/2002 | Fallin et al. | |
| 6,419,704 B1 | 7/2002 | Ferree | |
| 6,440,169 B1 | 8/2002 | Elberg et al. | |
| 6,447,546 B1 | 9/2002 | Bramlet et al. | |
| 6,451,019 B1 | 9/2002 | Zucherman et al. | |
| 6,451,020 B1 | 9/2002 | Zucherman et al. | |
| 6,458,131 B1 | 10/2002 | Ray | |
| 6,461,359 B1 | 10/2002 | Tribus et al. | |
| 6,471,704 B2 | 10/2002 | Gertzbein et al. | |
| 6,475,219 B1 | 11/2002 | Shelokov | |
| 6,478,796 B2 | 11/2002 | Zucherman et al. | |
| 6,481,440 B2 | 11/2002 | Gielen et al. | |
| 6,485,518 B1 | 11/2002 | Cornwall et al. | |
| 6,500,178 B2 | 12/2002 | Zucherman et al. | |
| 6,514,256 B2 | 2/2003 | Zucherman et al. | |
| 6,527,806 B2 | 3/2003 | Ralph et al. | |
| 6,540,747 B1 | 4/2003 | Marino | |
| 6,540,785 B1 | 4/2003 | Gill et al. | |
| 6,565,605 B2 * | 5/2003 | Goble et al. | 623/17.11 |
| 6,579,319 B2 | 6/2003 | Goble et al. | |
| 6,582,433 B2 | 6/2003 | Yun | |
| 6,585,769 B1 | 7/2003 | Muhanna et al. | |
| 6,610,091 B1 | 8/2003 | Reiley | |
| 6,616,669 B2 | 9/2003 | Ogilvie et al. | |
| 6,626,909 B2 | 9/2003 | Chin | |
| 6,626,944 B1 | 9/2003 | Taylor | |
| 6,652,527 B2 | 11/2003 | Zucherman et al. |
| 6,652,534 B2 | 11/2003 | Zucherman et al. |
| 6,652,585 B2 | 11/2003 | Lange |
| 6,669,729 B2 | 12/2003 | Chin |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,733,534 B2 | 5/2004 | Sherman |
| 6,761,719 B2 | 7/2004 | Justis et al. |
| 6,761,720 B1 | 7/2004 | Senegas |
| 6,783,527 B2 | 8/2004 | Drewry et al. |
| 6,796,983 B1 | 9/2004 | Zucherman et al. |
| 6,811,567 B2 | 11/2004 | Reiley |
| 6,835,205 B2 | 12/2004 | Atkinson et al. |
| 6,835,207 B2 | 12/2004 | Zacouto et al. |
| 7,087,084 B2 | 8/2006 | Reiley |
| 2001/0007073 A1 | 7/2001 | Zucherman et al. |
| 2001/0012938 A1 | 8/2001 | Zucherman et al. |
| 2001/0016743 A1 | 8/2001 | Zucherman et al. |
| 2001/0021850 A1 | 9/2001 | Zucherman et al. |
| 2001/0031965 A1 | 10/2001 | Zucherman et al. |
| 2001/0039452 A1 | 11/2001 | Zucherman et al. |
| 2002/0029039 A1 | 3/2002 | Zucherman et al. |
| 2002/0091446 A1 | 7/2002 | Zucherman et al. |
| 2002/0099384 A1 | 7/2002 | Scribner et al. |
| 2002/0116000 A1 | 8/2002 | Zucherman et al. |
| 2002/0123806 A1 | 9/2002 | Reiley |
| 2002/0143331 A1 | 10/2002 | Zucherman et al. |
| 2002/0151895 A1 | 10/2002 | Soboleski et al. |
| 2002/0183746 A1 | 12/2002 | Zucherman et al. |
| 2003/0004572 A1 | 1/2003 | Goble et al. |
| 2003/0009226 A1 | 1/2003 | Graf |
| 2003/0028250 A1 | 2/2003 | Reiley et al. |
| 2003/0040797 A1 | 2/2003 | Fallin et al. |
| 2003/0055427 A1 | 3/2003 | Graf |
| 2003/0065330 A1 | 4/2003 | Zucherman et al. |
| 2003/0073998 A1 | 4/2003 | Pagliuca et al. |
| 2003/0109880 A1 | 6/2003 | Shirado et al. |
| 2003/0153912 A1 | 8/2003 | Graf |
| 2003/0191470 A1 | 10/2003 | Ritland |
| 2003/0220642 A1 | 11/2003 | Freudiger |
| 2003/0220643 A1 | 11/2003 | Ferree |
| 2004/0006341 A1 | 1/2004 | Shaolian et al. |
| 2004/0006391 A1 | 1/2004 | Reiley |
| 2004/0024458 A1 | 2/2004 | Senegas et al. |
| 2004/0049189 A1 | 3/2004 | Le Couedic et al. |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0078082 A1 | 4/2004 | Lange |
| 2004/0082954 A1 | 4/2004 | Teitelbaum et al. |
| 2004/0087950 A1 | 5/2004 | Teitelbaum |
| 2004/0106995 A1 | 6/2004 | Le Couedic et al. |
| 2004/0111154 A1 | 6/2004 | Reiley |
| 2004/0116927 A1 | 6/2004 | Graf |
| 2004/0117017 A1 | 6/2004 | Pasquet et al. |
| 2004/0127989 A1 | 7/2004 | Dooris et al. |
| 2004/0143264 A1 | 7/2004 | McAfee |
| 2004/0147928 A1 | 7/2004 | Landry et al. |
| 2004/0153071 A1 | 8/2004 | Zucherman et al. |
| 2004/0158245 A1 | 8/2004 | Chin |
| 2004/0167520 A1 | 8/2004 | Zucherman et al. |
| 2004/0172025 A1 | 9/2004 | Drewry et al. |
| 2004/0181282 A1 | 9/2004 | Zucherman et al. |
| 2004/0181285 A1 | 9/2004 | Simonson |
| 2004/0186475 A1 | 9/2004 | Falahee |

| | | |
|---|---|---|
| 2004/0220568 A1 | 11/2004 | Zucherman et al. |
| 2004/0225289 A1 | 11/2004 | Biedermann et al. |
| 2004/0230192 A1 | 11/2004 | Graf |
| 2004/0230201 A1 | 11/2004 | Yuan et al. |
| 2004/0230304 A1 | 11/2004 | Yuan et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0243239 A1 | 12/2004 | Taylor |
| 2005/0010291 A1 | 1/2005 | Stinson et al. |
| 2005/0010293 A1 | 1/2005 | Zucherman et al. |
| 2005/0010298 A1 | 1/2005 | Zucherman et al. |
| 2005/0027361 A1 | 2/2005 | Reiley |
| 2005/0033434 A1 | 2/2005 | Berry |
| 2005/0033439 A1 | 2/2005 | Gordon et al. |
| 2005/0043797 A1* | 2/2005 | Lee ........................ 623/17.11 |
| 2005/0043799 A1 | 2/2005 | Reiley |
| 2005/0070899 A1 | 3/2005 | Doubler |
| 2005/0113927 A1 | 5/2005 | Malek |
| 2005/0119748 A1 | 6/2005 | Reiley et al. |
| 2005/0131406 A1 | 6/2005 | Reiley et al. |
| 2005/0137705 A1 | 6/2005 | Reiley |
| 2005/0137706 A1 | 6/2005 | Reiley |
| 2005/0143818 A1 | 6/2005 | Yuan et al. |
| 2005/0149190 A1 | 7/2005 | Reiley |
| 2005/0154467 A1 | 7/2005 | Peterman et al. |
| 2005/0171609 A1 | 8/2005 | Humphreys |
| 2005/0177166 A1 | 8/2005 | Timm |
| 2005/0267579 A1* | 12/2005 | Reiley et al. ............. 623/17.11 |
| 2006/0009847 A1* | 1/2006 | Reiley ..................... 623/17.11 |
| 2006/0084982 A1* | 4/2006 | Kim ............................ 606/61 |
| 2006/0149375 A1* | 7/2006 | Yuan et al. ............... 623/17.11 |
| 2006/0217718 A1 | 9/2006 | Chervitz |

FOREIGN PATENT DOCUMENTS

| | | |
|---|---|---|
| EP | 408489 A1 | 1/1991 |
| EP | 322334 B1 | 2/1992 |
| EP | 667127 A1 | 8/1995 |
| EP | 767637 B1 | 11/1998 |
| EP | 768843 B1 | 2/1999 |
| EP | 669109 B1 | 5/1999 |
| EP | 1299042 A2 | 4/2003 |
| EP | 1303224 A1 | 4/2003 |
| EP | 1303225 A1 | 4/2003 |
| EP | 1414358 A2 | 5/2004 |
| EP | 1448109 A2 | 8/2004 |
| EP | 1239785 B1 | 9/2004 |
| EP | 1343424 B1 | 9/2004 |
| EP | 1399078 B1 | 12/2004 |
| FR | 2721501 B1 | 8/1996 |
| JP | 10179622 A2 | 7/1998 |
| JP | 10277070 A2 | 10/1998 |
| SU | 1468543 A1 | 3/1989 |
| SU | 1517953 A1 | 10/1989 |
| WO | WO8707827 A1 | 12/1987 |
| WO | WO9421185 A1 | 9/1994 |
| WO | WO9505783 A1 | 3/1995 |
| WO | WO9505784 A1 | 3/1995 |
| WO | WO9505785 A1 | 3/1995 |
| WO | WO9505786 A1 | 3/1995 |
| WO | WO9600049 A1 | 1/1996 |
| WO | WO9822033 A1 | 5/1998 |
| WO | WO9848707 A1 | 11/1998 |
| WO | WO9848717 A1 | 11/1998 |
| WO | WO9856301 A1 | 12/1998 |
| WO | WO9905995 A1 | 2/1999 |
| WO | WO9921500 A1 | 5/1999 |
| WO | WO9921501 A1 | 5/1999 |
| WO | WO9923963 A1 | 5/1999 |
| WO | WO9965412 A1 | 12/1999 |
| WO | WO9960957 C2 | 5/2000 |
| WO | WO0038582 | 7/2000 |
| WO | WO0062684 A1 | 10/2000 |
| WO | WO0130248 A1 | 5/2001 |
| WO | WO0145576 A1 | 6/2001 |
| WO | WO0149192 A1 | 7/2001 |
| WO | WO0156489 A1 | 8/2001 |
| WO | WO0164142 A1 | 9/2001 |
| WO | WO0164144 A2 | 9/2001 |
| WO | WO0191657 A1 | 12/2001 |
| WO | WO0191658 A1 | 12/2001 |
| WO | WO0197721 A2 | 12/2001 |
| WO | WO0197721 A3 | 12/2001 |
| WO | W0207622 A1 | 1/2002 |
| WO | WO0200124 A1 | 1/2002 |
| WO | WO0203882 A2 | 1/2002 |
| WO | WO0207621 A1 | 1/2002 |
| WO | WO0207623 A1 | 1/2002 |
| WO | WO0213732 A3 | 2/2002 |
| WO | WO0230336 A2 | 4/2002 |
| WO | WO0234120 A2 | 5/2002 |
| WO | WO0243603 A1 | 6/2002 |
| WO | WO02067792 A2 | 9/2002 |
| WO | WO02067793 A2 | 9/2002 |
| WO | WO02089712 A1 | 11/2002 |
| WO | WO02089712 A2 | 11/2002 |
| WO | WO02102259 A2 | 12/2002 |
| WO | WO03009737 A1 | 2/2003 |
| WO | WO03011147 A1 | 2/2003 |
| WO | WO03015646 A2 | 2/2003 |
| WO | WO03045262 A2 | 6/2003 |
| WO | WO03077806 A1 | 9/2003 |
| WO | WO2004017817 A2 | 3/2004 |
| WO | WO2004019762 A2 | 3/2004 |
| WO | WO2004024010 A1 | 3/2004 |
| WO | WO2004032794 A2 | 4/2004 |
| WO | WO2004032794 A3 | 4/2004 |
| WO | WO2004039239 A2 | 5/2004 |
| WO | WO2004039239 A3 | 5/2004 |
| WO | WO2004039243 A2 | 5/2004 |
| WO | WO2004039243 A3 | 5/2004 |
| WO | WO2004041066 A2 | 5/2004 |
| WO | WO2004041066 A3 | 5/2004 |
| WO | WO2004073533 A1 | 9/2004 |
| WO | WO2004098423 A1 | 11/2004 |
| WO | WO2004098452 A1 | 11/2004 |
| WO | WO2004105577 A2 | 12/2004 |
| WO | WO2004105580 A2 | 12/2004 |
| WO | WO2005013864 | 2/2005 |
| WO | WO2005037149 | 4/2005 |
| WO | WO2005044152 A1 | 5/2005 |
| WO | WO2006102443 | 9/2006 |

OTHER PUBLICATIONS

Archus Orthopedics; *Total Facet Arthroplasty System (TFAS™)*. Website; http://www.archususa.com/Product.html.

Todd Anres; *Facet Joint Arthroplasty: A Glimpse of the Future of Spine Technology*, Othopaedic Product News, Sep./Oct. 2005 p. 38,40.

Shaw, M; Development of Artifical Facets- Biomechanical Perspective 51$^{st}$ Annual Meeting of the Orthopaedic Research Society, Poster No. 1263.

Goh JC, et al., "Influence of PLIF cage size on lumbar spine stability", Spine, Jan. 2000 25:1, PubMed abstract.

Head WC, Wagner surface replacement arthroplasty of the hip. Analysis of fourteen failures in forty-one hips; J Bone Joint Surg. [Am], Mar. 1981 63:3, PubMed Abstract.

Kotani Y, et al., "The effect of spinal fixation and destabilization on the biomechanical and histologic properties of spinal ligaments. An in vivo study.", Spine, Mar. 15, 1998 23:6, PubMed abstract.

Lemaire JP, et al., "Intervertebral Disc Prosthesis: Results and Prospects for the Year 2000", Clinical Orthopaedics and Related Research, PubMed abstract.

Nagata H, et al., "The effect of immobilization of long segments of the spine on the adjacent and distal facet force and lumbrosacral motion", Spine, Dec. 1993 18:16. PubMed abstract.

Nibu K, et al., Multidirectional stabilizing potential of BAK interbody spinal fusion system for anterior surgery, J Spinal Discord, Aug. 1997 10:4, PubMed abstract.

Tsantrizos A, et al., "Segmental stability and compressive strength of posterior lumbar interbody fusion implants", Spine, Aug. 1, 2000 25:15, PubMed abstract.

* cited by examiner

APPARATUS AND METHOD FOR POSTERIOR VERTEBRAL STABILIZATION

CROSS-REFERENCE TO RELATED APPLICATIONS

The following disclosure is incorporated herein by reference: U.S. application No. 10/860,778 filed Jun. 2, 2004 which carries Applicants' docket no. FSI-2 NPROV and is entitled SPINAL FACET IMPLANT WITH SPHERICAL IMPLANT APPOSITION SURFACE AND BONE BED AND METHODS OF USE.

BACKGROUND OF THE INVENTION

1. The Field of the Invention

The present invention relates generally to orthopedic medicine, and more precisely, to systems and methods for restricting relative motion between vertebrae.

2. The Relevant Technology

Many people experience back pain. Back pain is not only uncomfortable, but can be particularly debilitating. Many people who wish to participate in sports, manual labor, or even sedentary employment are unable to do so because of pains that arise from motion of or pressure on the spinal column. Such pains are often caused by traumatic, inflammatory, metabolic, synovial, neoplastic and degenerative disorders of the spine.

In order to alleviate such injuries and pains, spinal fusion techniques have been used for many years to essentially lock two vertebrae together. More recently, artificial discs have been used to replace natural intervertebral discs to correct disc pathologies, while still permitting the adjacent vertebrae to move with respect to each other. Various implants have also been proposed for the partial or complete replacement of vertebral facet joints to alleviate discomfort associated with diseased or atrophied articular processes, while still permitting intervertebral motion.

It has been discovered that excessive anterior/posterior motion between adjacent vertebrae can damage the associated intervertebral disc (i.e., "slip" the disc). Diseased or damaged spinal segments may be especially vulnerable to such damage to the intervertebral disc. Unfortunately, known spinal implants that permit some form of relative motion between the vertebrae generally do not sufficiently restrict the action of shear forces on the vertebrae.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention advances the state of the art by providing systems and methods that can be used to restrict relative anterior/posterior motion between adjacent vertebrae. The present invention can be used independently of other corrective procedures, but may advantageously be combined with replacement of one or more vertebral facets. The configuration and operation of selected embodiments of the invention will be shown and described in greater detail with reference to FIGS. 1 and 2, as follows.

Figure 1:
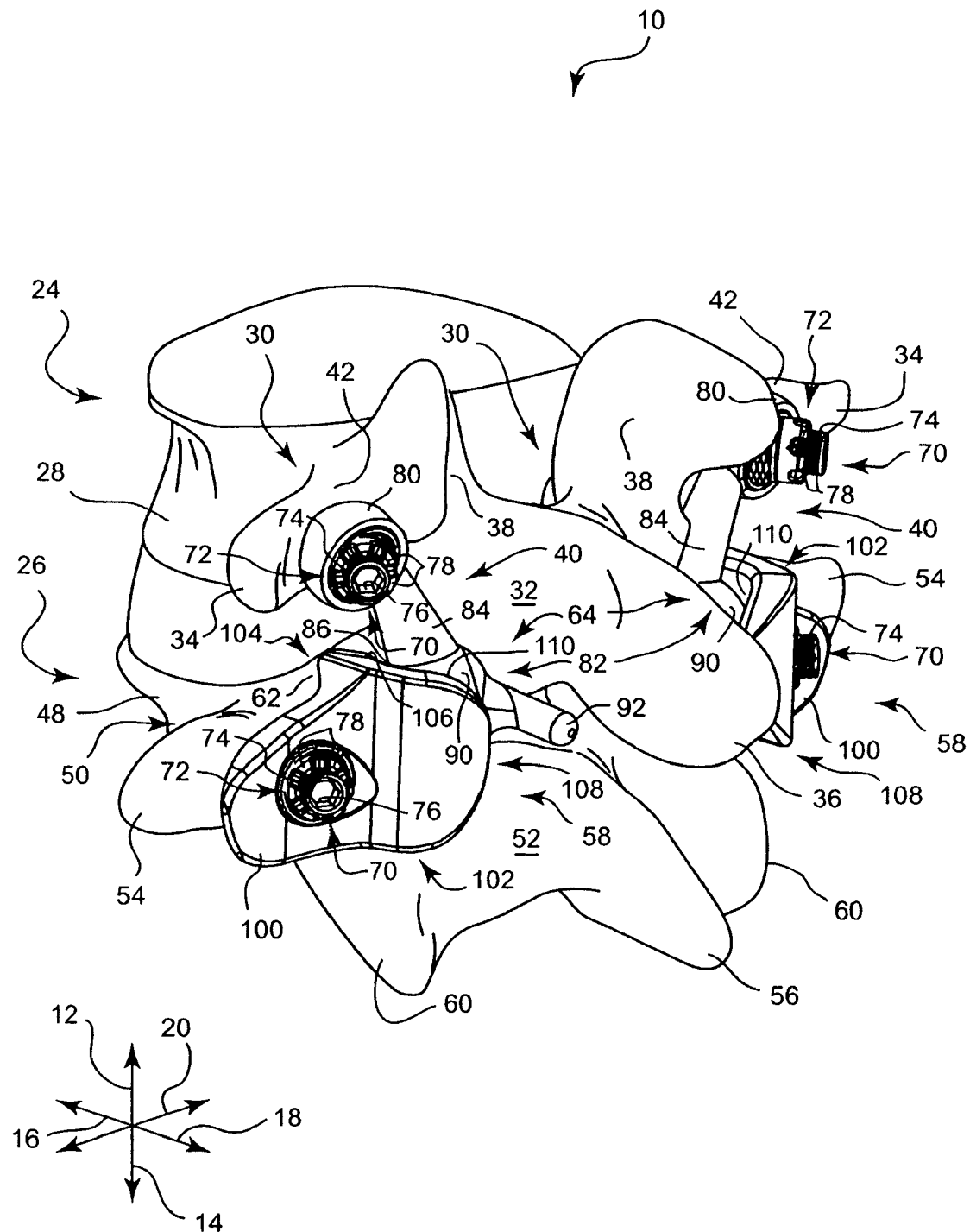
FIG. 1 is a perspective view of a portion of a spine including two vertebrae, on which an apparatus according to one embodiment of the invention is bilaterally installed.

Referring to FIG. 1, a perspective view illustrates a portion of a spine 10. FIG. 1 illustrates only the bony structures; accordingly, ligaments, cartilage, and other soft tissues are omitted for clarity. The spine 10 has a cephalad direction 12, a caudal direction 14, an anterior direction 16, a posterior direction 18, and a medial/lateral axis 20, all of which are oriented as shown by the arrows bearing the same reference numerals. In this application, "left" and "right" are used with reference to a posterior view, i.e., a view from behind the spine 10. "Medial" refers to a position or orientation toward a sagittal plane of the spine 10, and "lateral" refers to a position or orientation relatively further from the sagittal plane.

As shown, the portion of the spine 10 illustrated in FIG. 1 includes a first vertebra 24, which may be the L5 (Fifth Lumbar) vertebra of a patient, and a second vertebra 26, which may be the L4 (Fourth Lumbar) vertebra of the patient. The systems and methods may be applicable to any vertebra or vertebrae of the spine 10 and/or the sacrum (not shown). In this application, the term "vertebra" may be broadly interpreted to include the sacrum.

As shown, the first vertebra 24 has a body 28 with a generally disc-like shape and two pedicles 30 that extend posteriorly from the body 28. A posterior arch, or lamina 32, extends between the posterior ends of the pedicles 30 to couple the pedicles 30 together. The first vertebra 24 also has a pair of transverse processes 34 that extend laterally from the pedicles 30 generally along the medial/lateral axis 20, and a spinous process 36 that extends from the lamina 32 along the posterior direction 18.

The first vertebra 24 also has a pair of superior facets 38, which are positioned toward the top of the first vertebra 24 and face generally medially. The natural inferior facets (not shown) of the first vertebra 24 have been resected away, and a pair of inferior facet joint implants 40, or inferior implants 40, has been attached to the first vertebra 24 to replace the natural inferior articular surfaces. Each of the inferior implants 40 is attached to a saddle point 42 of the first vertebra 24. Each saddle point 42 is positioned generally at the center of the juncture of each superior facet 38 with the adjacent transverse process 34.

Similarly, the second vertebra 26 has a body 48 from which two pedicles 50 extend posteriorly. A posterior arch, or lamina 52, extends between the posterior ends of the pedicles 50 to couple the pedicles 50 together. The second vertebra 26 also has a pair of transverse processes 54 that extend from the pedicles 50 generally along the medial/lateral axis 20, and a spinous process 56 that extends from the lamina 52 along the posterior direction 18.

The natural superior facets (not shown) of the second vertebra 26 have been resected away, and a pair of superior facet replacement implants 58, or superior implants 58, has been attached to the second vertebra 26 to replace the natural superior articular surfaces. Additionally, the second vertebra 26 has inferior facets 60, which are positioned toward the bottom of the second vertebra 26 and face generally outward. Each of the superior implants 58 is attached to a saddle point 62 of the corresponding pedicle 50 of the second vertebra 26. Each saddle point 62 is positioned generally at the center of the juncture of the corresponding natural superior facet (not shown) with the adjacent transverse process 54.

The inferior implants 40 on the first vertebra 24 articulate (i.e., slide and/or press) with the superior implants 58 of the second vertebra 26 to limit relative motion between the first and second vertebrae 24, 26 in a manner similar to that of the resected natural articular surfaces. The combination of each inferior implant 40 with the adjacent superior implant 58 provides an apparatus 64 that operates as a prosthetic facet joint. The superior facets 38 of the first vertebra 24 and the inferior facets 60 of the second vertebra 26 are part of natural facet joints that control motion between the first and second vertebrae 24, 26 and adjacent vertebrae (not shown).

As shown, each of the implants 40, 58 is attached to the corresponding saddle point 42, 62 via a fixation member 70 and a castle nut 72. Each of the fixation members 70 may take the form of a pedicle screw, with a distal end having threads implanted in the corresponding pedicle 30 or 50 and a proximal end protruding therefrom, with threads 74 to receive the castle nuts 72 in threaded engagement. Each fixation member 70 has a torquing interface 76, such as the hexagonal recess illustrated in FIG. 1, which enables the fixation member 70 to be rotated into the implanted state through the use of a tool (not shown).

Each of the castle nuts 72 also has a torquing interface 78 that enables the castle nut 72 to be threaded snugly onto the threads 74 of the corresponding fixation member 70. The torquing interface 78 may take the form of crenelations encircling a bore through which the fixation member 70 may protrude. A tool (not shown) may engage the torquing interface 78 to help rotate the castle nut 72 into engagement with the threads 74 and tighten the castle nut 72 to grip the corresponding implant 40, 58 against the corresponding saddle point 42, 62.

The inferior implant 40 has a mounting portion 80, an articulation portion 82, and a stem 84. The mounting portion 80 is attached to the saddle point 42 of the first vertebra 24 via the corresponding fixation member 70 and castle nut 72. In the embodiment of FIG. 1, the mounting portion 80 has a generally semispherical shape that enables adjustment of the orientation of the inferior implant 40 against the saddle point 42 prior to tightening of the castle nut 72. The stem 84 extends from the mounting portion 80 to the articulation portion 82, which is positioned proximate the original location of the resected natural inferior facet.

The articulation portion 82 has an articular surface 86, an abutment surface 90, and a crosslinking extension 92. The articular surface 86 may be oriented generally laterally and anteriorly, like the natural inferior articular surface (not shown). The abutment surface 90 is oriented generally laterally and posteriorly. The crosslinking extension 92 extends almost directly posteriorly to receive a crosslink (not shown) to attach the articulation portions 82 together, thereby stabilizing the inferior implants 40 and ensuring that they do not slip against the first vertebra 24.

As also shown in FIG. 1, each of the superior implants 58 has a mounting portion 100 and an articulation portion 102. The mounting portion 100 may be attached to the corresponding saddle point 62 of the second vertebra 26. The articulation portion 102 is positioned proximate the original location of the resected natural articular surface (not shown). Since this is close to the saddle point 62, no stem is required to connect the mounting portion 100 to the articulation portion 102.

The articulation portion 102 has an anterior flange 104 with an articular surface 106 and a posterior flange 108 with a posterior stabilization surface 110. From the mounting portion 100, the anterior flange 104 protrudes generally anteriorly and medially, while the posterior flange 108 protrudes generally posteriorly and medially. The flanges 104, 108 of each superior implant 58 cooperate to generally encircle the lateral half of the articulation portion 82 of the corresponding inferior implant 40. The articular surface 106 faces and articulates with the articular surface 86 of the inferior implant 40. The posterior stabilization surface 110 faces and articulates with the abutment surface 90 of the inferior implant 40. The geometry of the articulation portions 82, 102 and the manner in which they articulate will be set forth in greater detail in connection with the discussion of FIG. 2.

Figure 2:
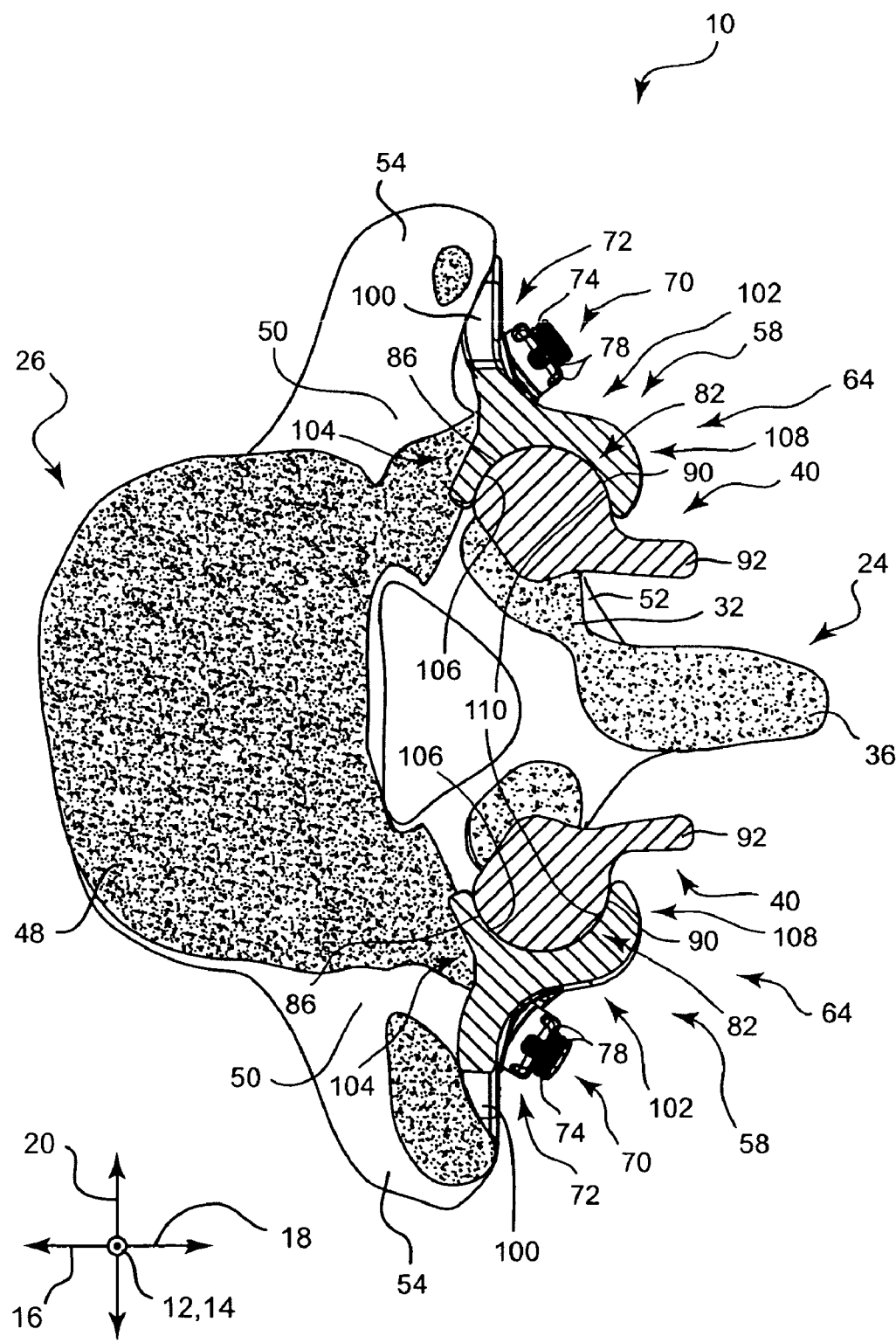
FIG. 2 is a caudal, section view of the vertebrae and the apparatus of FIG. 1.

Referring to FIG. 2, a cephalad, section view illustrates the portion of the spine 10 shown in FIG. 1 along with the bilateral apparatus 64 of FIG. 1. The section is taken just superior to the fixation members 70 and castle nuts 72 that attach the superior implant 58 to the second vertebra 26. Accordingly, only the inferior portion of the first vertebra 24 is visible, along with the articulation portions 82 of the inferior implants 40. The second vertebra 26 and the superior implants 58 are visible almost in their entirety.

As shown, the articular surface 86 and the abutment surface 90 of each inferior implant 40 cooperate to provide a substantially continuous, generally semicircular convex cross sectional shape, with the articular surface 86 facing generally laterally and anteriorly, while the abutment surface 90 faces generally laterally and posteriorly. The articular surface 106 and the posterior stabilization surface 110 of each superior implant 58 similarly cooperate to provide a continuous, generally semicircular concave cross sectional shape. The articular surface 106 faces generally medially and posteriorly, while the posterior stabilization surface 110 faces generally medially and anteriorly.

Accordingly, the articular surfaces 106 articulate with the articular surfaces 86 to restrict anterior and medial/lateral motion of the first vertebra 24 with respect to the second vertebra 26. The articular surfaces 106, 86 are shaped to cooperate to replicate the articulation of a natural facet joint; accordingly, the articular surfaces 106, 86 may permit sufficient anterior and medial/lateral motion of the first vertebra 24 with respect to the second vertebra 26 to enable relatively natural flexion, extension, rotation, and lateral bending of the spine 10. To this end, the articular surfaces 106, 86 are shaped in such a manner that relative cephalad/caudal motion is generally unrestricted.

The articular surfaces 106, 86 generally do not restrict posterior motion of the first vertebra 24 with respect to the second vertebra 26. Thus, if the posterior flanges 108 of the superior implants 58 were not present, the first vertebra 24 would be able to relatively freely move posteriorly with respect to the second vertebra 26. Excessive relative anterior/posterior motion would place excessive shearing forces on the intervertebral disc between the first and second vertebrae 24, 26, and potentially injure the intervertebral disc.

The abutment surface 90 and the posterior stabilization surface 110 cooperate to substantially prevent this condition. The abutment surface 90 cooperates with the posterior stabilization surface 110 to restrict posterior motion of the first vertebra 24 with respect to the second vertebra 26. The posterior stabilization surface 110 may thus replicate the growth that occurs posteriorly of many natural superior facet joints to prevent such relative motion.

As illustrated in FIG. 2, the posterior stabilization surface 110 is generally trough-shaped. A "trough-shaped" surface is a surface with opposing sides that are upraised to define a central channel. A trough-shaped surface may be a linearly extruded surface, such as a sectional portion of a cylindrical surface, like the posterior stabilization surface 110 of FIG. 2. A linearly extruded surface is a surface that has substantially the same cross section along a linear length, as though the surface has been formed by extrusion through an opening having the cross-sectional shape. Alternatively, a trough-shaped surface may have a cross sectional shape that remains constant over a nonlinear path, or that does not remain constant over any path at all. A trough-shaped surface may also be a surface of revolution, i.e., a shape rotated through at least a portion of a circular path.

In the alternative to a trough-like shape, a posterior stabilization surface may have any of a wide variety of shapes. Such a surface may have a substantially planar shape, a semispherical shape, a parabolic shape, or a shape defined by more complex mathematical constructs, or any combination thereof.

In the embodiment of FIG. 2, the posterior stabilization surface 110 is substantially continuously formed with the articular surface 106 of the anterior flange 104. Surfaces that are "substantially continuous" with each other are generally surfaces that are not separated by a corner, edge, or break. In alternative embodiments (not shown), a posterior stabilization surface or an abutment surface need not be substantially continuous with an articular surface. Rather, a posterior stabilization surface or abutment surface may be discontinuous from, or even entirely detached from, the corresponding articular surface.

In FIG. 2, the articular surfaces 106, 86 are shown with substantially no play between them. Similarly, the abutment surface 90 and the posterior stabilization surface 110 are illustrated with substantially no play. However, when the first and second vertebrae 24, 26 are moved to different relative positions, as when flexion, extension, rotation, or lateral bending has occurred, more play may be present between the articular surfaces 106, 86 and/or between the abutment surface 90 and the posterior stabilization surface 110. Indeed, in alternative embodiments, gaps may exist between the articular surfaces 106, 86 and/or between the abutment surface 90 and the posterior stabilization surface 110 in all relative dispositions of the vertebrae 24, 26, depending on the range of motion to be allowed by the implants 40, 58. Notably, the implants 40, 58 do permit significant extension of the first and second vertebrae 24, 26.

In yet another alternative embodiments, a wide variety of other structures could be used to restrict posterior motion of a superior vertebra relative to an inferior vertebra. For example, a posterior stabilization surface may be positioned on a flange extending from an inferior implant (not shown), rather than on a superior implant. Such an implant may abut an abutment surface positioned on a superior implant (not shown).

According to other alternative embodiments, a posterior stabilization surface may abut a natural vertebral surface rather than an abutment surface of a second implant. Hence, an implant may be used to limit relative posterior motion of a superior vertebra even if only one or more superior or inferior implants are used. Such implants may then articulate with natural bone structures such as natural articular surfaces. In this application, an articular surface on a vertebra includes both prosthetic and natural articular surfaces.

In other alternative embodiments (not shown), a posterior stabilization surface may be incorporated into a kinematic feature, such as a linkage, that restricts posterior motion of the superior vertebra. In yet another alternative embodiments (not shown), a resilient mechanism such as a spring could be provided and situated such that posterior motion of the superior vertebra can be more gradually and gently restricted. Those of skill in the art will recognize that a wide variety of other alternative embodiments may be constructed within the scope of the present invention.

The present invention has particular relevance to orthopedic medicine, and more particularly to facet joint replacement. However, the principles, structures, and methods of the present invention may be utilized independently of facet joint replacement methods and devices.

The present invention may be embodied in other specific forms without departing from its spirit or essential characteristics. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An apparatus for replacing at least a portion of a facet joint to limit relative motion between a first vertebra and a second vertebra adjacent to the first vertebra, the apparatus comprising:
  a first prosthesis comprising:
    a first fixation portion configured to be attached to the first vertebra;
    a first articular surface connected to the first fixation portion; and
    a posterior stabilization surface having a rigid structure; and
  a second prosthesis comprising:
    a second fixation portion configured to be attached to the second vertebra; and
    a second articular surface connected to the second fixation portion;
  wherein, upon attachment of the first and second fixation portions to the first and second vertebrae, the first and second articular surfaces are shaped and positioned to articulate with each other,
  the posterior stabilization surface is shaped and positioned to receive contact from the second prosthesis to limit motion of a superior vertebra of the first and second vertebrae in a posterior direction with respect to an inferior vertebra of the first and second vertebrae, and the first and second articular surfaces and the posterior stabilization surface are shaped and positioned to permit unrestricted relative motion of the first and second vertebrae in extension.

2. The apparatus of claim 1, wherein the first prosthesis is monolithic, wherein the first articular surface is shaped to replace a natural superior facet of the first vertebra, and the second articular surface is shaped to replace an inferior articular surface of the second vertebra.

3. The apparatus of claim 2, wherein the posterior stabilization surface extends substantially medially from a posterior portion of the first articular surface.

4. The apparatus of claim 2, wherein the first articular surface is generally trough-shaped, wherein the posterior stabilization surface is substantially continuous with the first articular surface.

5. The apparatus of claim 1, wherein the posterior stabilization surface comprises at least one of the group consisting of a substantially planar surface, a cylindrical surface, a linearly extruded surface, and a surface of revolution.

6. The apparatus of claim 1, wherein the second prosthesis further comprises an abutment surface positioned such that, upon attachment of the first and second fixation portions to the first and second vertebrae, the abutment surface contacts the posterior stabilization surface in response to posterior motion of a superior vertebra of the first and second vertebrae with respect to an inferior vertebra of the first and second vertebrae.

7. The apparatus of claim 1, wherein the posterior stabilization surface is positioned to substantially avoid restricting relative motion of the first and second vertebrae in flexion, extension, rotation, and lateral bending.

8. An apparatus for replacing at least a portion of a facet joint to limit relative motion between a first vertebra and a second vertebra adjacent to the first vertebra, the apparatus comprising:
a first prosthesis comprising:
a first fixation portion configured to be attached to the first vertebra;
a first articular surface connected to the first fixation portion; and
a posterior stabilization surface comprising at least one of the group consisting of a substantially planar surface, a cylindrical surface, a linearly extruded surface, and a surface of revolution; and
a second prosthesis comprising:
a second fixation portion configured to be attached to the second vertebra; and
a second articular surface connected to the second fixation portion;
wherein, upon attachment of the first and second fixation portions to the first and second vertebrae, the first and second articular surfaces are shaped and positioned to articulate with each other,
the posterior stabilization surface is shaped and positioned to receive contact from the second prosthesis to limit motion of a superior vertebra of the first and second vertebrae in a posterior direction with respect to an inferior vertebra of the first and second vertebrae,
and the first articular surface comprises a trough shape oriented to extend cephalad-caudally and open at the cephalad and caudal ends.

9. The apparatus of claim 8, wherein the first articular surface is shaped to replace a natural superior facet of the first vertebra, and the second articular surface is shaped to replace an inferior articular surface of the second vertebra.

10. The apparatus of claim 9, wherein the posterior stabilization surface extends substantially medially from a posterior portion of the first articular surface.

11. The apparatus of claim 9, wherein the first prosthesis is monolithic, wherein the posterior stabilization surface is substantially continuous with the first articular surface.

12. The apparatus of claim 8, wherein the second prosthesis further comprises an abutment surface positioned such that, upon attachment of the first and second fixation portions to the first and second vertebrae, the abutment surface contacts the posterior stabilization surface in response to posterior motion of a superior vertebra of the first and second vertebrae with respect to an inferior vertebra of the first and second vertebrae.

13. The apparatus of claim 8, wherein the posterior stabilization surface is positioned to substantially avoid restricting relative motion of the first and second vertebrae in flexion, extension, rotation, and lateral bending.

14. A method comprising:
positioning a first articular surface of a first prosthesis proximate an original location of a natural articular surface of a first vertebra;
positioning a second articular surface of a second prosthesis proximate an original location of a natural articular surface of a second vertebra to enable the first articular surface to articulate with the second articular surface;
positioning a posterior stabilization surface of the first prosthesis to receive contact from the second prosthesis to limit motion of a superior vertebra of the first and second vertebrae in a posterior direction with respect to an inferior vertebra of the first and second vertebrae and, in cooperation with the first and second articular surfaces, to permit unrestricted relative motion of the first and second vertebrae in extension;
securing the first prosthesis to the first vertebra; and
securing the second prosthesis to the second vertebra.

15. The method of claim 14, wherein the natural articular surface of the first vertebra comprises a natural superior facet, wherein the second articular surface is shaped to replace an inferior articular surface of the second vertebra.

16. The method of claim 15, wherein the posterior stabilization surface extends substantially medially from a posterior portion of the first articular surface.

17. The method of claim 15, wherein the first prosthesis is monolithic, wherein the first articular surface is generally trough-shaped, wherein the posterior stabilization surface is substantially continuous with the first articular surface.

18. The method of claim 14, wherein the posterior stabilization surface comprises at least one of the group consisting of a substantially planar surface, a cylindrical surface, a linearly extruded surface, and a surface of revolution.

19. The method of claim 14, wherein the second prosthesis further comprises an abutment surface, the method further comprising: positioning the abutment surface to contact the posterior stabilization surface in response to posterior motion of a superior vertebra of the first and second vertebrae with respect to an inferior vertebra of the first and second vertebrae.

20. The method of claim 14, wherein positioning the posterior stabilization surface comprises substantially avoiding restriction of relative motion of the first and second vertebrae in flexion, extension, rotation, and lateral bending.

\* \* \* \* \*